United States Patent
Hsieh et al.

(10) Patent No.: US 7,706,497 B2
(45) Date of Patent: Apr. 27, 2010

(54) METHODS AND APPARATUS FOR NOISE ESTIMATION FOR MULTI-RESOLUTION ANISOTROPIC DIFFUSION FILTERING

(75) Inventors: Jiang Hsieh, Brookfield, WI (US); Jean-Baptiste Thibault, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 12/049,128

(22) Filed: Mar. 14, 2008

(65) Prior Publication Data

US 2009/0232269 A1 Sep. 17, 2009

(51) Int. Cl.
*A61B 6/00* (2006.01)
(52) U.S. Cl. .......................... 378/5; 378/98.12
(58) Field of Classification Search .......... 378/4, 378/5, 98.11, 98.12
See application file for complete search history.

(56) References Cited

U.S. PATENT DOCUMENTS

| | | | | |
|---|---|---|---|---|
| 4,463,375 A | * | 7/1984 | Macovski | 378/98.12 |
| 4,503,461 A | * | 3/1985 | Nishimura | 378/98.12 |
| 6,493,416 B1 | * | 12/2002 | Hsieh | 378/4 |
| 2008/0095462 A1 | | 4/2008 | Hsieh et al. | |

OTHER PUBLICATIONS

K.Z. Abd-Elmoniem et al., Real-Time Speckle Reduction and Coherence Enhancement in Ultrasound Imaging via Nonlinear Anisotropic Diffusion, IEEE Transactions on Biomedical Engineering, vol. 49, No. 9, Sep. 2002.

* cited by examiner

*Primary Examiner*—Edward J Glick
*Assistant Examiner*—Alexander H Taningco
(74) *Attorney, Agent, or Firm*—Dean Small; Small Patent Law Group

(57) ABSTRACT

A method for reducing noise in a computed tomographic (CT) image includes acquiring both a first set of projection views and a second set of projection views, wherein for each projection view in the first set of projection views there is an associated projection view in the second set of projection views representing the same object scanned at substantially the same time from substantially the same position. The method further includes reconstructing the first set of projection views and the associated second set of projection views to obtain a first image and a second image, respectively. Next, the first image and the second image are combined to obtain a noise map and an amount of noise in a product image is estimated utilizing the noise map. The method also includes filtering using the noise map to perform noise reduction.

20 Claims, 5 Drawing Sheets

METHODS AND APPARATUS FOR NOISE ESTIMATION FOR MULTI-RESOLUTION ANISOTROPIC DIFFUSION FILTERING

BACKGROUND OF THE INVENTION

This invention relates generally to computed tomographic (CT) imaging, and more particularly to methods and apparatus for noise reduction in CT imaging applications.

Dose reduction has been the focus of research for x-ray CT for many years. By reducing the noise in the reconstructed images, either or both of the x-ray intensity used for scanning or the duration of a scan can be reduced, thereby reducing the dose to a patient while maintaining the same image quality as a scan without the benefit of noise reduction. It is well known that noise reduction can be performed either in projection space or in image space. Speckle reduction methods based on anisotropic diffusion have been proposed to reduce noise, but these methods are computationally intensive and are not able to keep up with the high frame rates of today's scanners.

Improvements of the speckle reductions methods were later proposed as a multi-scale version of anisotropic diffusion. A dyadic wavelet method has been used in some CT imaging applications to decompose the image into different image scales. Although these previously proposed methods are sufficient for ultrasound applications, they cannot be implemented directly for CT applications. One of the major obstacles to implementation of the methods in CT is the estimation of the noise property in the image. The anisotropic diffusion method uses an equation written as:

$$\frac{\partial I(x, y, t)}{\partial t} = div[d(\|\nabla I\|) \cdot \nabla I] \quad (1)$$

where $\|\nabla I\|$ denotes the local gradient, and $d(\|\nabla I\|)$ the diffusivity function. The function $d(\|\nabla I\|)$ should be monotonically decreasing so that diffusion decreases as the gradient strength increases. One such function is $$d(u) = e^{-\frac{u^2}{2\sigma_n^2}} \quad (2)$$

The parameter $\sigma_n$ depends upon the noise in the image. In ultrasound imaging, the noise can be either a constant for a particular type of the clinical exam, or the minimum standard deviation measured across the entire image. However, the use of a constant as a noise estimate does not yield satisfactory results for CT because noise changes significantly in CT from pixel to pixel as a result of the anatomical change.

What is needed are faster, more efficient methods and apparatus for reducing noise in CT imaging applications.

BRIEF DESCRIPTION OF THE INVENTION

In one aspect, some embodiments of the present invention provide a method for reducing noise in a computed tomographic (CT) image. The method includes acquiring both a first set of projection views and a second set of projection views, wherein for each projection view in the first set of projection views there is an associated projection view in the second set of projection views representing the same object scanned at substantially the same time from substantially the same position. The method further includes reconstructing the first set of projection views and the associated second set of projection views to obtain a first image and a second image, respectively. Next, the first image and the second image are combined to obtain a noise map and an amount of noise in a product image is estimated utilizing the noise map. The method also includes filtering using the noise map to perform noise reduction.

In another aspect, some embodiments of the present invention provide a computed tomographic imaging apparatus that is configured to perform the methods described herein. The apparatus includes a radiation source and a radiation detector on a rotating gantry. The radiation detector is configured to receive radiation from the radiation source through an object being scanned. The apparatus further includes a computer, a data acquisition system configured to receive data from the radiation detector when the computed tomographic imaging apparatus is scanning an object and to provide projection datasets to the computer, and a display responsive the computer for displaying images produced by the computer from the projection datasets.

In yet another aspect, some embodiments of the present invention provide a machine readable medium or media on which is/are recorded instructions to perform the methods described herein.

DETAILED DESCRIPTION OF THE INVENTION

Figure 1:
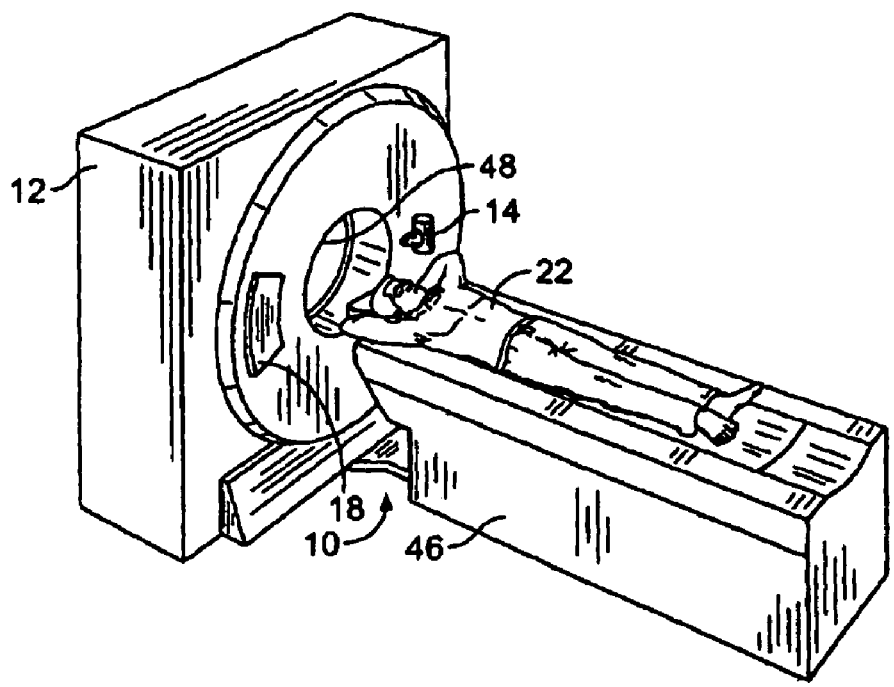
FIG. 1 is drawing of an embodiment of a CT imaging apparatus.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings, nor are the figures necessarily drawn to scale.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Additionally, the recitation of a particular number of elements does not exclude embodiments having more than that particular number, unless the number is further qualified by words such as "exactly" or "only." Also, unless the possibility is either explicitly, logically, or physically excluded, individual features may be omitted from an embodiment, or one or more features from another embodiment or other embodiments, may be combined to produce additional embodiments of the present invention.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image. Additionally, although described in detail in a CT medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Technical effects of embodiments of the present invention include noise reduction in images produced by scanned CT imaging applications, even when the objects being imaged are scanned using a high-speed CT scanners. Yet another technical effect achieved by embodiments of the present invention is a reduction in complexity and increase in speed of low-noise image reconstruction from scanned CT image data. The manner in which these and other technical effects of embodiments of the present invention are achieved will become apparent to one of ordinary skill in the art upon achieving an understanding of the inventive subject matter taught herein.

In some known CT imaging system configurations, a radiation source projects a fan-shaped beam is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Figure 2:
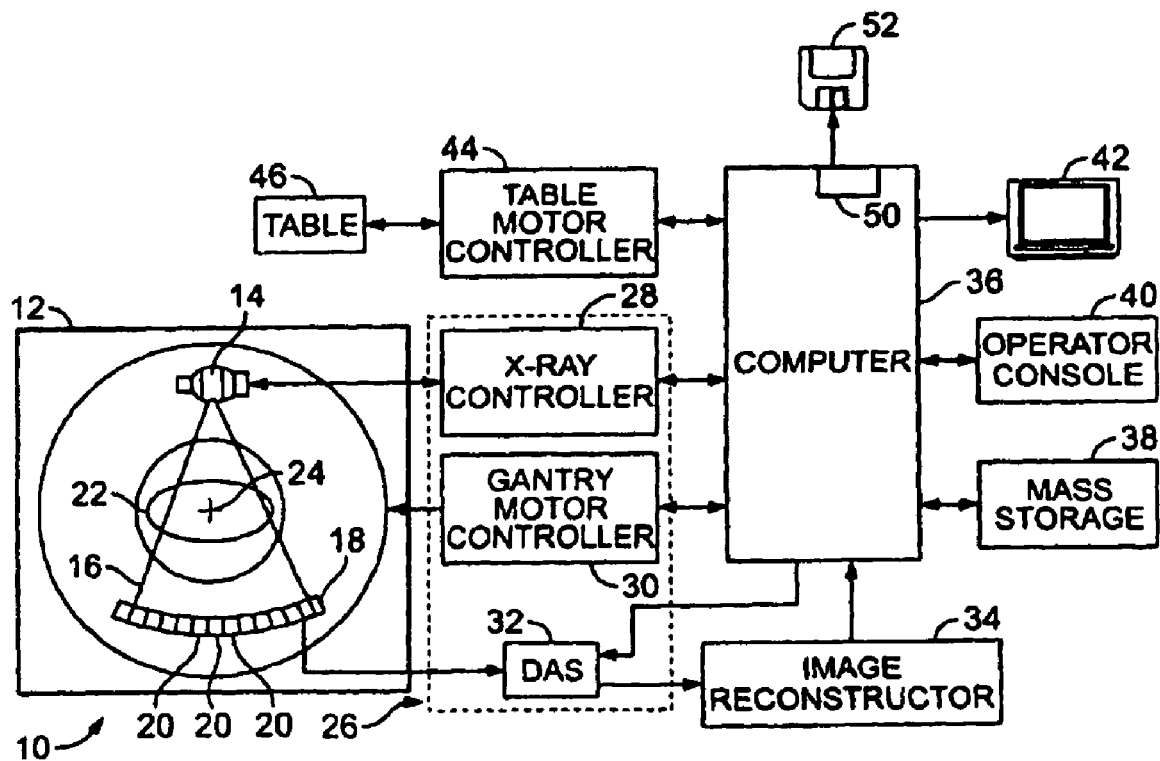
FIG. 2 is a pictorial block diagram of the CT imaging apparatus of FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown) including a plurality of detector elements 20 that together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a mass storage device 38.

Computer 36 also receives commands and scanning parameters from an operator via console 40 that has a keyboard and/or other user input device(s). An associated display system 42 allows the operator to observe the reconstructed image and other data from computer 36. The operator supplied commands and parameters are used by computer 36 to provide control signals and information to DAS 32, radiation controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, or DVD-ROM drive, for reading instructions and/or data from a computer-readable medium 52, such as a floppy disk, CD-ROM, or DVD. It should be understood that other types of suitable computer-readable memory are recognized to exist (e.g., CD-RW and flash memory, to name just two), and that this description is not intended to exclude any of these. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
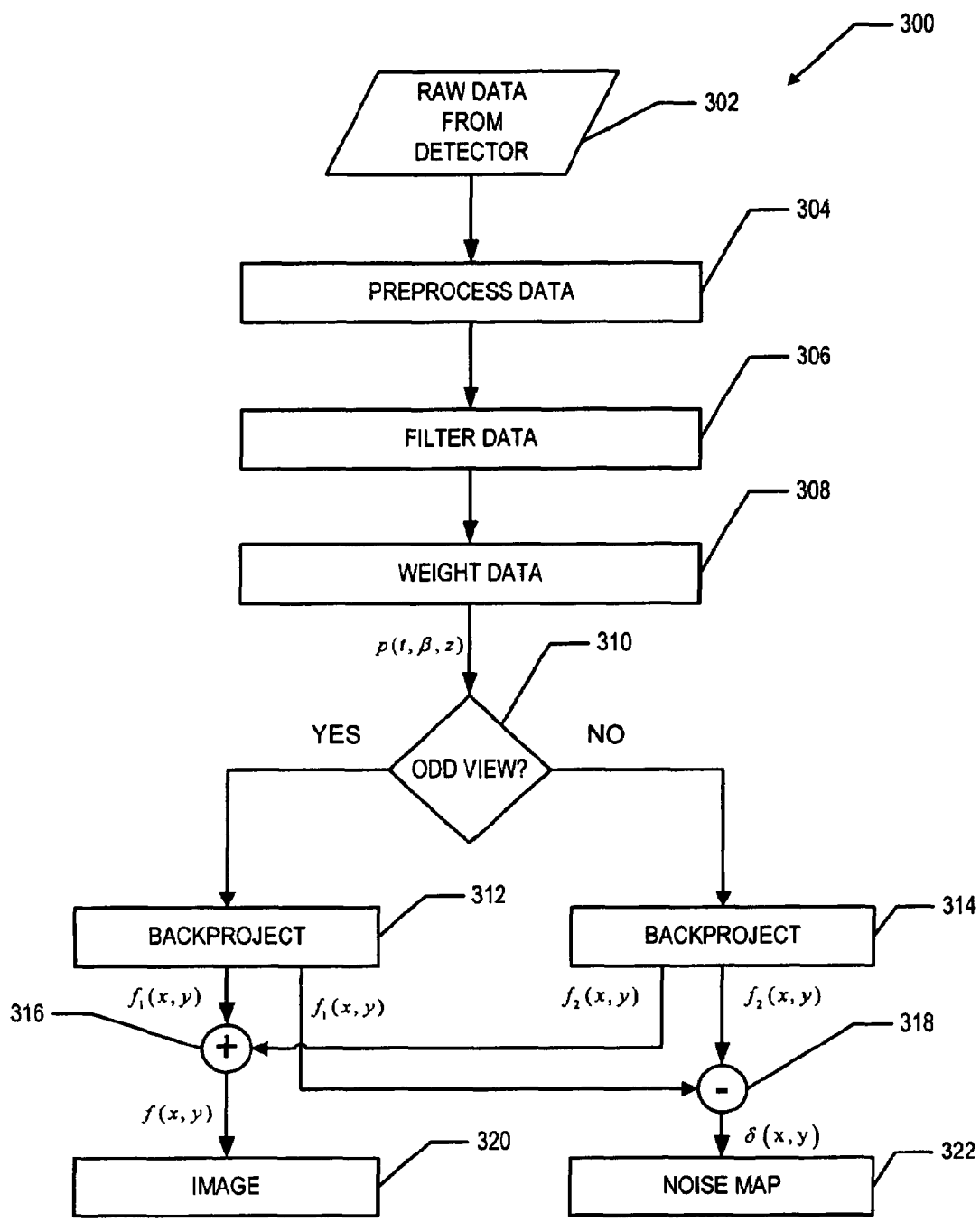
FIG. 3 is a flow chart illustrating an embodiment of a method of the present invention.

To simplify the noise estimation process, some embodiments of the present invention utilize a method illustrated by flowchart 300 of FIG. 3. For each projection dataset, raw data acquired from a detector at 302 is subjected to standard preprocessing and calibration at 304, filtering at 306, and weighting at 308 as usual, for example, using processes or methods known to those skilled in the art. However, after these standard procedures are performed, the weighted and filtered projection p(t,β,z) is then split into a plurality of groups. In the embodiment illustrated in flowchart 300, the projection data is separated into two groups. In some embodiments, this separation is dependent upon whether the view is an even or odd view at 310, with odd views backprojected at 312 to an image $f_1(x,y)$ and even views backprojected at 314 to another image $f_2(x,y)$. Note that the designations "odd" and "even" are somewhat arbitrary, in that it does not matter which view is the initial view as long as the views alternate between odd and even. In other configurations of the present invention, the first group is a first set of projection views and the second group is a second set of projection views representing the same object scanned at substantially the same time from substantially the same position. In some other configurations of the present invention, the first set of projection views and the second set of projection views are obtained using radiation at different energies.

Because the two sets of projections (even and odd) are collected in a high speed scanner at essentially the same time (e.g., less than a millisecond timing difference between an odd view and the associated even view), the reconstructed images $f_1(x,y)$ and $f_2(x,y)$ represent the same object 22 scanned at essentially the same time and essentially from the same position. Therefore, the difference between the images $f_1(x,y)$ and $f_2(x,y)$ represents variation due to noise rather than anatomical structure. Because backprojection is a linear operation, the summation f(x,y) of the two images $f_1(x,y)$ and $f_2(x,y)$ is an image 320 identical to an image reconstructed without the advantages of embodiments of the present invention. The variation due to noise δ(x,y) can be produced at 322 (e.g., producing a noise map) by taking the difference between the two images:

$$f(x,y)=f_1(x,y)+f_2(x,y)$$

$$\delta(x,y)=f_1(x,y)-f_2(x,y) \quad (3)$$

Figure 4:
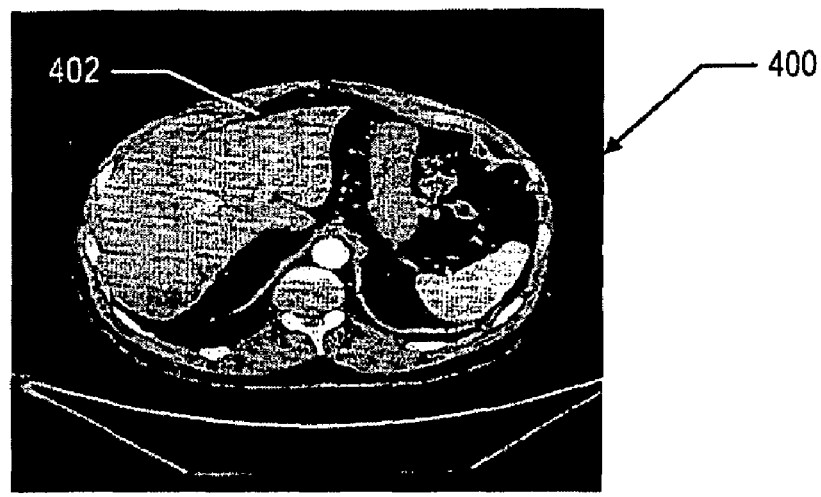
FIG. 4 is an image of a patient liver study.
Figure 5:
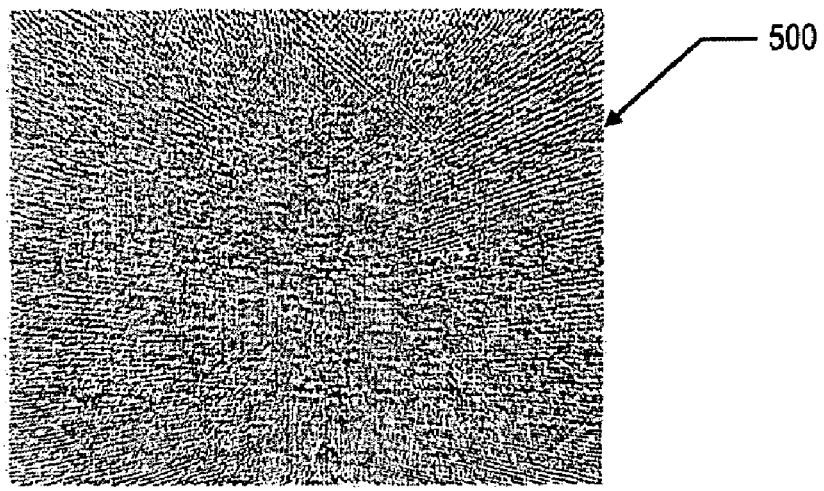
FIG. 5 is a noise map generated using an embodiment of the method illustrated in the flow chart of FIG. 3.

FIG. 4 and FIG. 5 show an example of a patient liver study image 400 and noise map 500, respectively. It is clear from the figure that no anatomical structure 402 is present in noise map 500. This fact serves as a confirmation for the noise map generation because the estimated noise map should not include real object structures that are to be preserved.

The terminology "noise map" is used to describe the quantity δ(x,y) instead of the noise because δ(x,y) provides only a good estimation of the noise and is not the standard deviation itself. To estimate the standard deviation σ(x,y) in the original image, an operation written as follows is performed:

$$\sigma(x, y) = \frac{1}{\sqrt{2}N}\sqrt{\sum_{y=1}^{N}\sum_{x=1}^{N}[\delta(x,y)-\overline{\delta}(x,y)]^2}, \quad (4)$$

where $\overline{\delta}$ is the mean of δ(x,y) over an N×N neighborhood. By changing the size parameter N, the resulting standard deviation function essentially undergoes a smooth operation to suppress statistical fluctuations or artifacts. This operation is computationally intensive. Other embodiments determine a scaled version of the smoothed noise map written as:

$$\sigma(x, y) = \xi(x, y) \otimes \sum_{y=1}^{N}\sum_{x=1}^{N}|\delta(x,y)| \quad (5)$$

Additional low-pass filtering can be applied to the function δ(x,y) to further suppress fluctuations due to the presence of aliasing artifacts or other statistical fluctuations. With the noise estimation, anisotropic diffusion filtering can be performed.

In another embodiment, instead of calculating two images from the even and odd projection views, two images from two half-scans are used to estimate the noise. For example, in a step-and-shoot mode of data acquisition, projection data from 0 to 2π is obtained for reconstruction. An image $f_1(x, y)$ is generated using the projection from the first halfscan (0, π+fan angle), and a second image, $f_2(x, y)$ is generated from the second halfscan (π−fan angle, 2π). The two images then undergo the same operation as illustrated in Eqs. (3)-(4) and processes described in the previous paragraphs to produce the original image and the noise map. Similarly, when data is collected in a small helical pitch (approximately equal to 1 or smaller than 1), two images are generated from substantially disjointed projections (one from the first portion of the helical and the other from the second portion of the helical) and similar treatment are used to produce the image and the noise map.

Although the above methods provide noise improvements, given the significant noise challenges of some modern scanners, the demand for noise reduction has significantly increased. Therefore, a two-dimensional anisotropic diffusion filter is expanded in some embodiments of the present invention to achieve even greater noise reduction. There are several methods by which three-dimensional filtering can be performed. One of these methods includes modification of equation (1) to include the z-dimension of the reconstructed volume:

$$\frac{\partial I(x, y, z, t)}{\partial t} = div[d(\|\nabla I\|) \cdot \nabla I] \quad (8)$$

Although this method is straightforward, its computational complexity is high and quality improvement is related to the complexity of parameter tweaking and convergence speed. Therefore, some embodiments of the present invention utilize multiple two-dimensional filtering instead of direct 3D filtering. One such method includes performing three 2D filtering operations, namely, the same 2D filtering operation in the x-y plane, x-z plane, and y-z plane. If $f_{x-y}(x,y,z)$, $f_{y-z}(x,y,z)$, and $f_{x-z}(x,y,z)$ denote the filtered images in three planes, the final image $f_{x-y-z}(x,y,z)$ can be obtained by combining three image volumes:

$$f_{x-y-z}(x,y,z) = G[f_{x-y}(x,y,z), f_{x-z}(x,y,z), f_{y-z}(x,y,z)] \quad (9)$$

where G is a general function. For example, G can be a simple averaging operator where the mean of the three filtered volumes is calculated. G can also be a median filter operator where the median values of the three filtered volumes are used as the final image.

Figure 6:
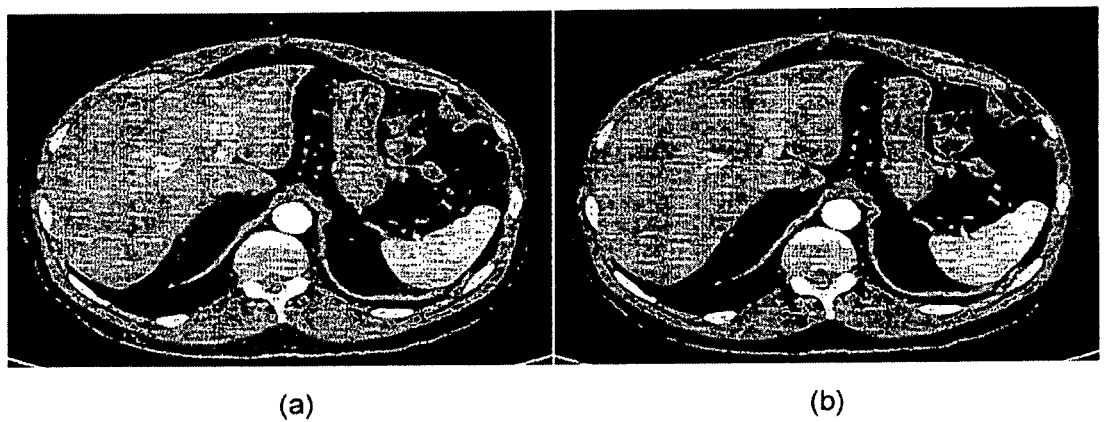
FIG. 6 is a patient liver study showing an original image (a) and an image (b) improved using an embodiment of the present invention.

FIG. 6 shows a patient liver study reconstructed using a known reconstruction method (a) and using an embodiment of the present invention (b). A significant reduction in noise is achieved by using one of more embodiments of the present invention. At the same time, no or little resolution loss is encountered.

Special handling of the noise map generation due to aliasing artifacts may be desirable when the filter cutoff frequency is high. For example, because the frequency of the aliasing artifacts can be determined based on the cutoff frequency and the trigger frequency, a notch filter is provided in some embodiments to separate the aliasing artifacts from the real noise map. In some embodiments, the $\xi(x,y)$ function in equation (5) is used to suppress aliasing artifact contribution.

Various alternatives can be used for the 3D filtering implementation. For example, the 2D wavelet transform (plane-by-plane) is combined or interchanged in some embodiments with a 3D diffusion method in which each voxel is smoothed according to the values of its neighbors in 3D and the local statistics.

Figure 7:
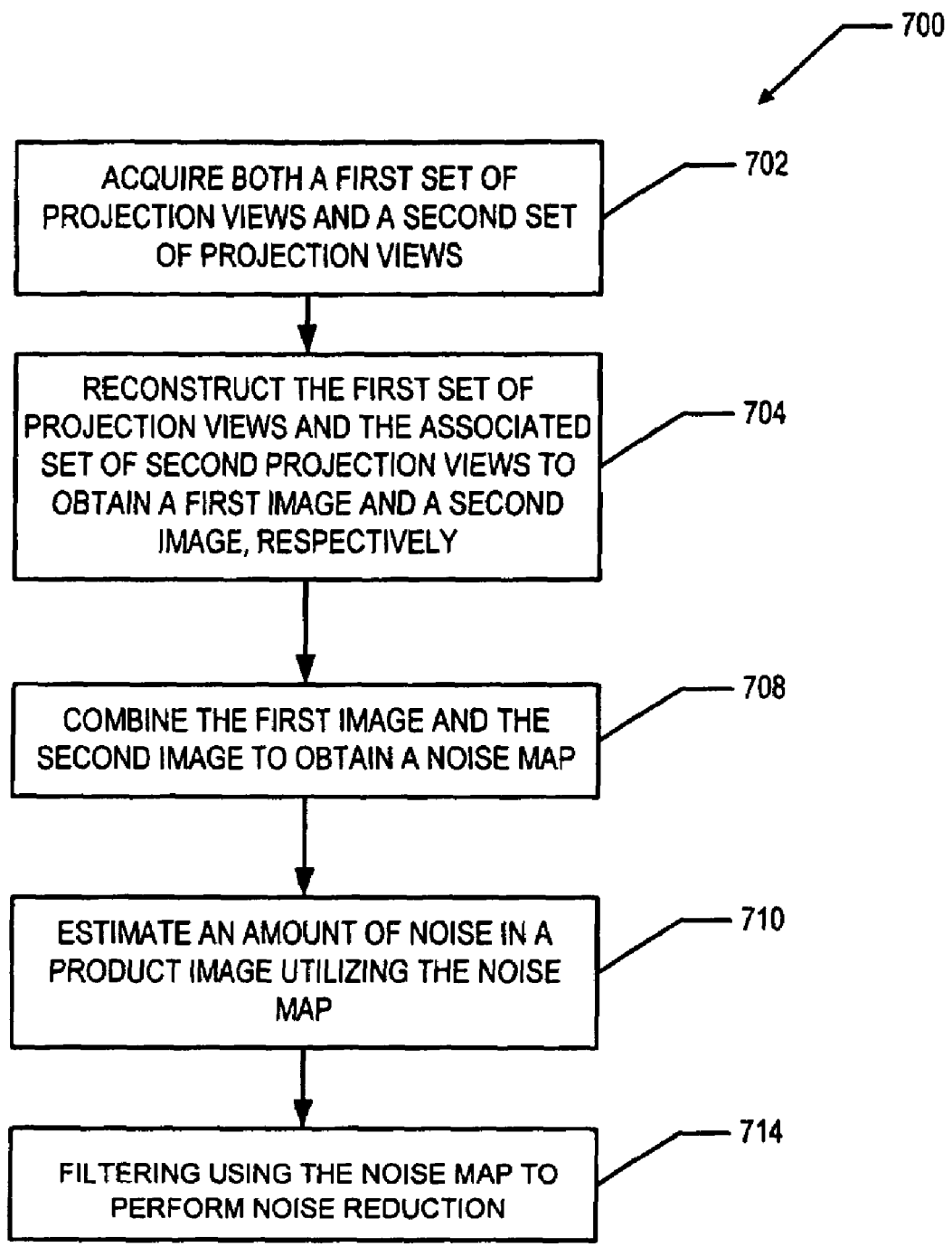
FIG. 7 is a flow chart of one method embodiment of the present invention.

A summary of a method used in various embodiments of the present invention is provided by flow chart 700 of FIG. 7. In particular, a method for reducing noise in a computed tomographic (CT) image is provided. The method includes acquiring, at 702, both a first set of projection views and a second set of projection views, wherein for each projection view in the first set of projection views there is an associated projection view in the second set of projection views representing the same object scanned at essentially the same time from essentially the same position. In some embodiments of the present invention, the first set of projection views and the second set of projection views are (not necessarily respectively) a set of even projection views and a set of odd projection views. In other embodiments, the first set of projection views and the second set of projection views are (not necessarily respectively) a first portion of a projection dataset and a second portion of a projection dataset. In yet other embodiments, the first set of collection views and the second set of projection views are collected using radiation from a radiation source at different energies or kVps.

The method next includes, at 704, reconstructing the first set of projection views and the associated set of second projection views to obtain a first image and a second image, respectively. Continuing at 708, the method then includes combining the first image and the second image to obtain a noise map. At 710, the method further includes estimating an amount of noise in a product image utilizing the noise map. Finally, at 714, the method includes filtering using the noise map to perform noise reduction.

In some embodiments, the combining of the three image volumes includes determining a mean of the three image volumes. Also in some embodiments, the combining of the three image volumes further comprises determining a median of the three image volumes.

In some embodiments of the present invention, aliasing artifacts are separated from the noise map. Also in some embodiments, a scaled version of the noise map (or, in some embodiments, a filtered version of the noise map) is used to suppress aliasing artifacts. Filtering the noise map to perform noise reduction can include filtering in 3D, wherein the 3D filtering includes smoothing voxels in accordance with the value of neighboring voxels and local statistics. In yet other embodiments filtering the noise map to perform noise reduction can include performing a 2D filtering in three perpendicular planes to obtain three image volumes and combining the three imaging volumes to obtain a final image. The filtering provided at 714 can include either a 3D filtering or a 2D filter, and apparatus embodiments of the present invention can provide either type of filtering, or both types, but embodiments of the present invention are not required to provide both types of filtering.

In some embodiments of the present invention, the first projection view and the associated second projection view are acquired less than a millisecond apart. Also in some embodiments, acquiring both an even set of projection views and an odd set of projection views includes acquiring projection views of a liver of a patient.

In yet other embodiments, a computed tomographic imaging apparatus 10 is provided that is configured to perform one or more of the methods above. CT imaging apparatus 10 includes radiation source 14 and radiation detector 18 on rotating gantry 12, the radiation detector 18 is configured to receive radiation 16 from the radiation source 14 through an object 22 being scanned, computer 36, data acquisition system 32 configured to receive data from the radiation detector when computed tomographic imaging apparatus 10 is scanning object 22 and to provide projection datasets to computer 36, and display 42 responsive the computer for displaying images produced by the computer from the projection datasets.

In yet another embodiment of the present invention, instructions to perform method embodiments of the present invention are provided on a machine readable medium or media 52.

In yet another embodiment of the present invention, a plurality of focal spots (such as a plurality of x-ray sources 14) are present in CT imaging apparatus 10. These x-ray focal spots emit x-rays 16 in a sequential manner in some embodiments (one spot emitting x-rays following the emission from its neighboring spot) or in a non-sequential order in other embodiments. Some embodiments can emit x-rays in either manner. Because of the redundant samples produced by the plurality of x-ray spots (each path is sampled a plurality of times over a short time period), a plurality of sets of projection data can be obtained and a plurality of images are generated from these projections. Noise maps are then estimated in accordance with the plurality of images of a single object location, such as a part of a patient's anatomy.

In yet another embodiment of the present invention, dual energy (or multi-energy) acquisition is performed. One such acquisition is the so-called fast kV switching in which a high-voltage generator switches quickly between two kV settings (e.g., 80 kVp and 140 kVp) so that projection views alternate between the two energy settings. To equalize x-ray statistics, the high-kVp is collected over one projection sample, and the low-kVp is collected over two or more projection samples. Because of the small number of samples of the high-kVp views, in conventional imaging systems, it is often difficult to implement an even-odd view method to generate a noise map. However, the even-odd views of the low-kVp are used in some embodiments of the present invention to generate a noise map, which is then scaled for the high-kVp noise estimation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for reducing noise in a computed tomographic (CT) image, said method comprising:
   acquiring both a first set of projection views and a second set of projection views, wherein for each projection view in the first set of projection views there is an associated projection view in the second set of projection views representing the same object scanned at substantially the same time from substantially the same position;
   reconstructing the first set of projection views and the associated second set of projection views to obtain a first image and a second image, respectively;
   combining the first image and the second image to obtain a noise map;
   estimating an amount of noise in a product image utilizing the noise map; and
   filtering using the noise map to perform noise reduction.

2. The method of claim 1 wherein the first set of projection views and the second set of projection views are a set of even projection views and a set of odd projection views.

3. The method of claim 1 wherein the first set of projection views and the second set of projection views are a first portion of a projection dataset and a second portion of a projection dataset.

4. The method of claim 1 further comprising collecting the first set of collection views and the second set of projection views using radiation at different energies.

5. The method of claim 1 further comprising performing a 2D filtering in three perpendicular planes to obtain three image volumes and combining the three image volumes to obtain a final image.

6. The method of claim 5 wherein the combining of the three image volumes further comprises determining a mean of the three image volumes.

7. The method of claim 5 wherein the combining of the three image volumes further comprises determining a median of the three image volumes.

8. The method of claim 1 further comprising reducing aliasing artifacts from the noise map.

9. The method of claim 1 further comprising using at least one of a scaled version of the noise map and a filtered version of the noise map.

10. The method of claim 1 further comprising filtering in 3D, said filtering comprising smoothing voxels in accordance with the value of neighboring voxels and local statistics.

11. A computed tomographic imaging apparatus comprising a radiation source and a radiation detector on a rotating gantry, the radiation detector configured to receive radiation from the radiation source through an object being scanned, a computer, a data acquisition system configured to receive data from the radiation detector when the computed tomographic imaging apparatus is scanning an object and to provide projection datasets to the computer, and a display responsive the computer for displaying images produced by the computer from the projection datasets,
   said computed tomographic imaging apparatus configured to:
   acquire both a first set of projection views and a second set of projection views, wherein for each projection view in the first set of projection views there is an associated projection view in the second set of projection views representing the same object scanned at substantially the same time from substantially the same position;
   reconstruct the first set of projection views and the associated second set of projection views to obtain a first image and a second image, respectively;
   combine the first image and the second image to obtain a noise map;
   estimate an amount of noise in a product image utilizing the noise map; and
   filter using the noise map to perform noise reduction.

12. The apparatus of claim 11 wherein the first set of projection views and the second set of projection views are a set of even projection views and a set of odd projection views.

13. The apparatus of claim 11 wherein the first set of projection views and the second set of projection views are a first portion of a projection dataset and a second portion of a projection dataset.

14. The apparatus of claim 1 wherein the radiation source is a variable energy radiation source, and said apparatus further configured to collect the first set of collection views and the second set of projection views using radiation at different energies of the variable energy radiation source.

15. The apparatus of claim 11 further configured to perform a 2D filtering in three perpendicular planes to obtain three image volumes and to combine the three image volumes to obtain a final image.

16. The apparatus of claim 15 wherein to combine the three image volumes, said apparatus further configured to determine a mean of the three image volumes.

17. The apparatus of claim 15 wherein to combine the three image volumes, said apparatus further configured to determine a median of the three image volumes.

18. The apparatus of claim 11 further configured to use at least one of a scaled version of the noise map and a filtered version of the noise map.

19. The apparatus of claim 11 having a plurality of radiation sources configured to emit radiation in at least one of a sequential manner and a non-sequential manner to obtain a plurality of sets of projection data and to generate a plurality of images from these projections, and to estimate noise in accordance with the plurality of images at a single location of the object.

20. A machine-readable medium or media having recorded thereon instructions configured to instruct a computer having operative access to a first set of projection views and a second set of projection views representing an object, wherein for each projection view in the first set of projection views there is an associated projection view in the second set of projection views representing the same object scanned at substantially the same time from substantially the same position, to:
    reconstruct the first set of projection views and the associated second set of projection views to obtain a first image and a second image, respectively;
    combine the first image and the second image to obtain a noise map;
    estimate an amount of noise in a product image utilizing the noise map; and
    filter using the noise map to perform noise reduction.

* * * * *